(12) United States Patent
Ventimiglia et al.

(10) Patent No.: US 7,563,794 B2
(45) Date of Patent: Jul. 21, 2009

(54) ZIPRASIDONE FREE FROM COLORED IMPURITIES AND A PROCESS FOR ITS PREPARATION

(75) Inventors: Gianpiero Ventimiglia, Cinisello Balsamo (IT); Pietro Allegrini, San Donato Milanese (IT); Gabriele Razzetti, Sesto S. Giovanni (IT); Domenico Magrone, Milan (IT); Alberto Bologna, Crema (IT)

(73) Assignee: Dipharma Francis S.r.l., Baranzate (Milan) (IT)

( * ) Notice: Subject to any disclaimer, the term of this patent is extended or adjusted under 35 U.S.C. 154(b) by 371 days.

(21) Appl. No.: 11/368,677

(22) Filed: Mar. 7, 2006

(65) Prior Publication Data

US 2006/0211708 A1 Sep. 21, 2006

(30) Foreign Application Priority Data

Mar. 7, 2005 (IT) .......................... MI2005A0346

(51) Int. Cl.
*A61K 31/497* (2006.01)
*C07D 413/00* (2006.01)
*C07D 417/00* (2006.01)
*C07D 419/00* (2006.01)

(52) U.S. Cl. .................. 514/254.04; 544/368
(58) Field of Classification Search ............ 514/254.04; 544/368
See application file for complete search history.

(56) References Cited

U.S. PATENT DOCUMENTS

2004/0048876 A1 * 3/2004 Busch et al. ........... 514/254.04
2006/0089502 A1 * 4/2006 Venkataraman et al. ..... 544/368

* cited by examiner

*Primary Examiner*—James O Wilson
*Assistant Examiner*—Erich A Leeser
(74) *Attorney, Agent, or Firm*—Young & Thompson

(57) ABSTRACT

Ziprasidone base or a pharmaceutically acceptable salt thereof free from colored impurities, in particular those giving the product a "slightly pink to pink" coloration.

1 Claim, 2 Drawing Sheets

ZIPRASIDONE FREE FROM COLORED IMPURITIES AND A PROCESS FOR ITS PREPARATION

FIELD OF THE INVENTION

The present invention relates to ziprasidone base, or a pharmaceutically acceptable salt thereof, free from colored impurities; and a purification process for the preparation thereof.

TECHNOLOGICAL BACKGROUND

Ziprasidone hydrochloride, namely 5-(2-(4-(1,2-benzisothiazol-3-yl)-1-piperazinyl)-ethyl)-6-chloro-1,3-dihydro-2H-indol-2-one hydrochloride, of formula

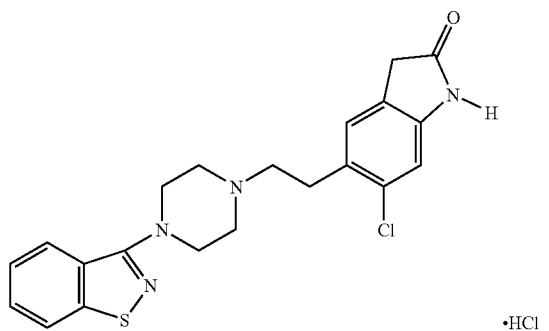

is used as an antipsychotic. Its preparation is known from U.S. Pat. No. 4,831,031. Ziprasidone base and its pharmaceutically acceptable salts are pink in color, in fact Merck Index Online® reports that anhydrous ziprasidone hydrochloride is a "white to slightly pink powder". The pink coloration, most likely due to highly coloring impurities, is present even in highly pure ziprasidone, for instance with purity above 99.9%. The pink coloration of the powders is a severe problem in the pharmaceutical chemistry, in that the APIs (Active Pharmaceutical Ingredients) should be free from coloring impurities to satisfy regulatory requirements. To date, efforts to remove said coloring impurities using, for example, adsorption on charcoal, have been dissatisfying. There is therefore the need for ziprasidone free from any coloring impurities.

Ziprasidone hydrochloride shows high permeability through biological membranes, which is favourable in terms of bioavailability. EP 965 343 reports that ziprasidone hydrochloride is sparingly water-soluble and, when obtained in the form of particles having diameter lower than or equal to 85, μm at least 70% of the compound dissolves within 45 minutes in aqueous solutions at physiological pH, independently of the particle size. Anhydrous ziprasidone hydrochloride is highly hygroscopic, in fact when exposed to air it spontaneously converts to the hydrate form. Particles of anhydrous ziprasidone hydrochloride with diameter lower than or equal to 85 μm still maintain high hygroscopicity, which affects work up, transportation, storage and formulation of pharmaceutical forms. There is therefore the need for anhydrous ziprasidone hydrochloride in form of particles having improved resistance to absorption of atmospheric humidity.

SUMMARY OF THE INVENTION

It has now been found a process which provides ziprasidone base and its pharmaceutically acceptable salts, free from colored impurities, and therefore white, so as to fulfil regulatory requirements. Furthermore, it has been found that anhydrous ziprasidone hydrochloride in the form of particles having mean diameter D[4,3] higher than 85 μm shows improved resistance to atmospheric humidity, keeping substantially unchanged its water solubility and therefore its bioavailability. This greatly reduces the problems connected with hygroscopicity and allows its advantageous use in therapy.

BRIEF DISCLOSURE OF THE FIGURES

Figure 1:
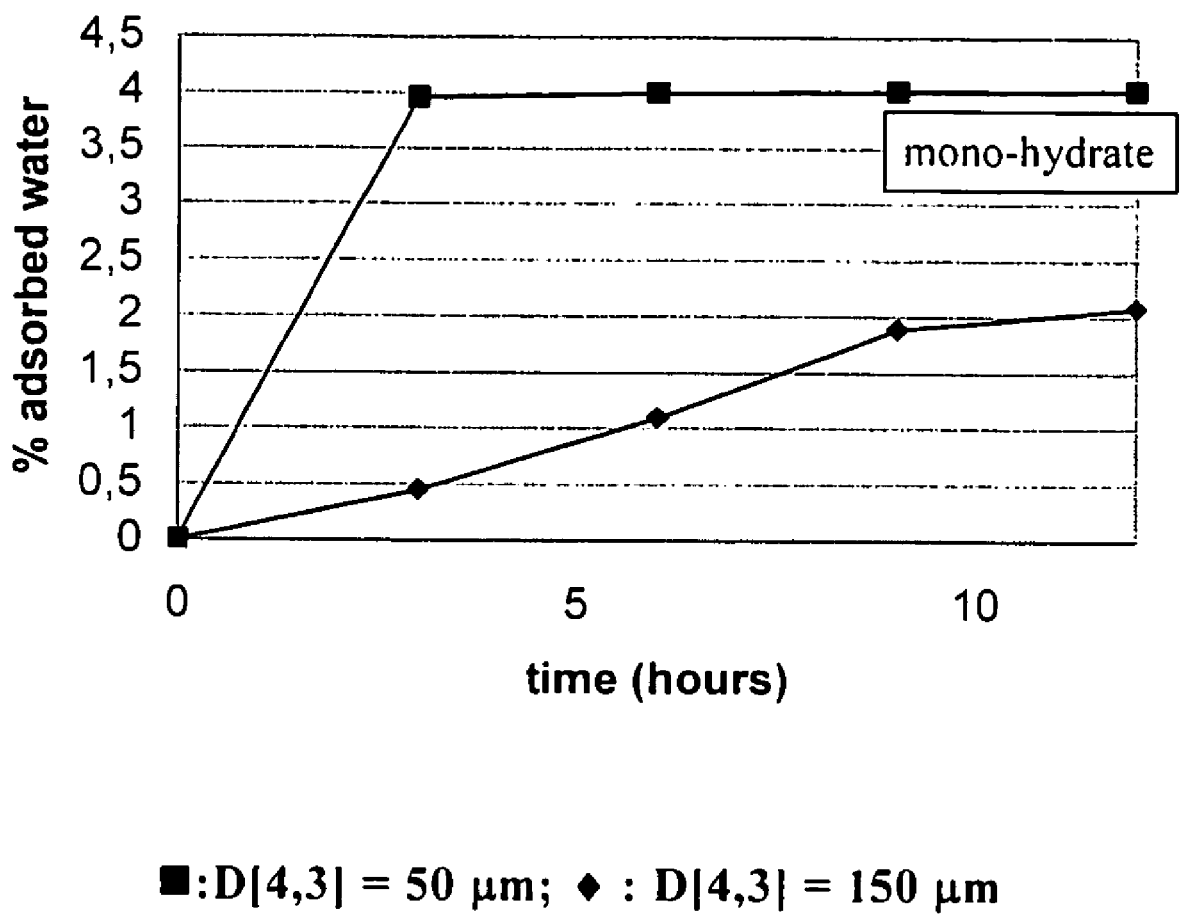

FIG. 1. Particle size distribution curve of an anhydrous ziprasidone hydrochloride sample having mean diameter larger than 85 μm, particular of about 150 μm.

Figure 2:
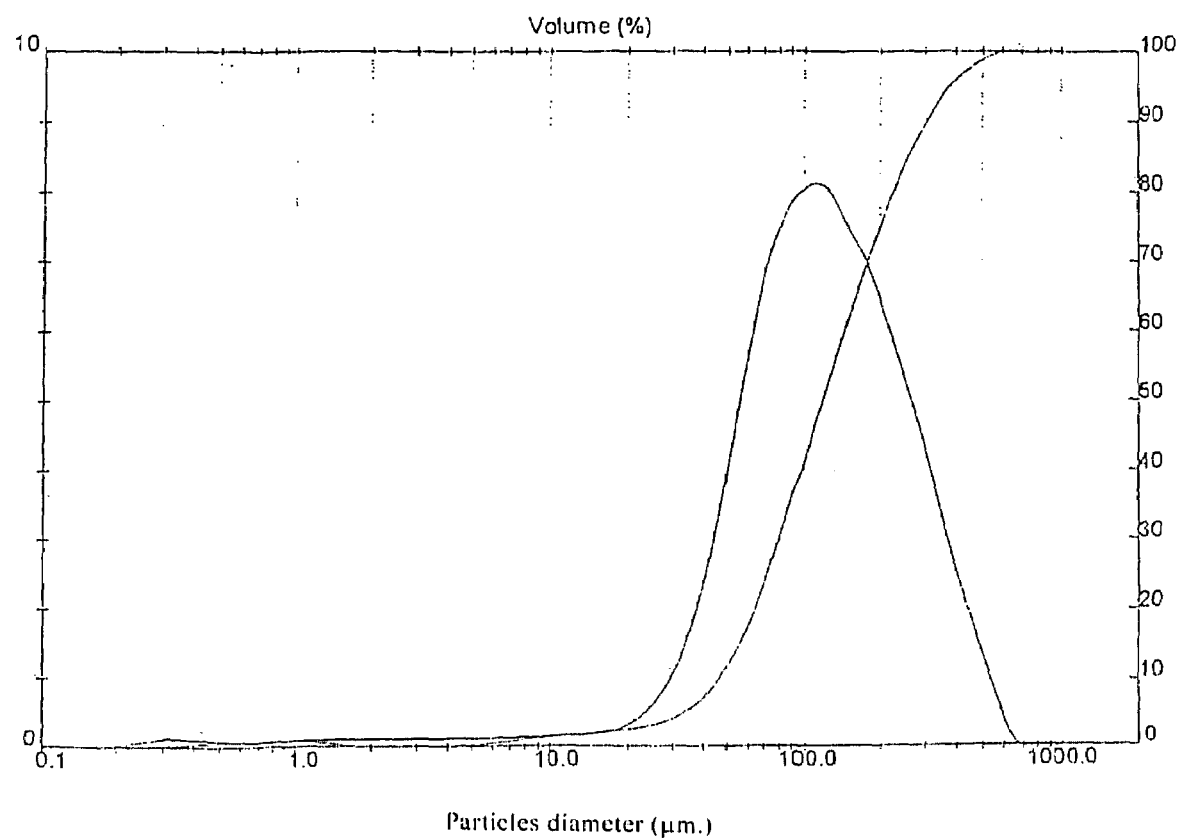

FIG. 2. Comparison between data concerning water absorption for two anhydrous ziprasidone hydrochloride samples, having mean diameter of 50 μm and 150 μm, respectively.

According to the present invention, the term "particle" means a single entity, both as a single and geminate crystal.

The statement that a sample of particles has mean diameter, referred to as D[4,3], higher than X μm, means that the mean of the volumes of the particles forming the sample is higher than the volume of a spherical particle with X diameter.

$D_{10}$ means that 10% by volume of the particles sample have diameter below the specified value.

Particles size, mean diameter "D[4,3]" and $D_{10}$ were determined with the known laser light scattering technique using a Malvern Mastersizer MS1 instrumentation under the following operative conditions:

300RF mm lens with of 2.4 mm laser beam length;
sample of 500 mg dispersed in 10 ml of hexane (reagent ACS) with 1% SPAN 85®, without presonication, and 2500 rpm stirring rate.

The samples water content was determined by the known Karl—Fischer technique. "Approximatively" and "about" herein mean around ±10% of the indicated value.

DETAILED DISCLOSURE OF THE INVENTION

The object of the present invention is ziprasidone base or a pharmaceutically acceptable salt thereof free from colored impurities, in particular those giving the product a "slightly pink to pink" coloration.

A ziprasidone pharmaceutically acceptable salt is typically a salt with a physiologically acceptable acid, in particular the hydrochloride and the mesylate.

The term ziprasidone base, or a pharmaceutically acceptable salt thereof, herein means the product both in the amorphous and crystalline form, and both in the anhydrous and hydrate form. An example of a preferred anhydrous form is anhydrous ziprasidone hydrochloride, disclosed in U.S. Pat. No. 5,321,925. Examples of preferred hydrate forms are ziprasidone hydrochloride hemi-hydrate and monohydrate, known from U.S. Pat. No. 4,831,031 and U.S. Pat. No. 5,321,925; and the ziprasidone mesylate di-hydrate and tri-hydrate forms known from U.S. Pat. No. 6,110,918 and WO 97/42191.

A second object of the invention is a process for the preparation of ziprasidone base, or a pharmaceutically acceptable salt thereof, free from colored impurities, comprising:

preparation of a ziprasidone free base dispersion in a polar protic organic solvent;

preparation of a ziprasidone addition salt by reaction of ziprasidone free base with an organic acid;

separation and recovery of the resulting addition salt;

preparation of crystalline ziprasidone hydrochloride by displacing the organic acid by reaction with hydrochloric acid in water-alcohol mixture;

recovery of anhydrous ziprasidone hydrochloride and, if desired, conversion to ziprasidone free base and/or, if desired, to another pharmaceutically acceptable salt thereof.

A polar protic organic solvent is typically an alkanol, in particular a $C_1$-$C_6$ alkanol, selected e.g. from methanol, ethanol, 1-propanol, 2-propanol, 1-butanol, 2-butanol, preferably methanol or ethanol, more preferably methanol.

The concentration of ziprasidone free base in the starting dispersion preferably ranges from 5 to 9% approxiniatively, more preferably from 6 to 8% approximatively.

The temperature of the dispersion approximatively ranges from 0° C. to the boiling temperature of the solvent used, preferably approx from 50° C. to the boiling temperature.

The resulting dispersion is heated and added with an organic acid dispersion in a polar protic solvent, selected e.g. from one of above listed alkanols, under stirring. Examples of organic acids are sulfonic acids, in particular methanesulfonic, ethanesulfonic, β-hydroxyethanesulfonic, p-toluenesulfonic, naphthalenesulfonic and camphorsulfonic acids. More preferred examples are methanesulfonic and camphorsulfonic acids, most preferably camphorsulfonic acid, both as a single (R) or (S) enantiomer and as a racemic mixture. The product ziprasidone camphorsulfonate, both as a single (R) or (S) enantiomer and as a racemic mixture, is novel and is an object of the invention.

After the addition of the organic acid, the corresponding addition salt separates from the dispersion upon cooling, and it can be recovered by conventional techniques, typically by filtration or centrifugation, followed by washing with the same solvent as used in the preparation procedure and optional final drying under vacuum at a temperature ranging from 50° C. to the boiling temperature of the solvent used in the preparation procedure.

A dispersion of said addition salt is prepared in a water-alcohol mixture, wherein the alkanol is selected from those listed above, and is preferably the same alkanol as used in the preceding step. Preferred examples of water-alcohol mixtures are methanol-water and ethanol-water, more preferably methanol-water. The alcoholic solvent percentage in the water-alcohol mixture can approximatively range from 70 to 90% v/v.

The concentration of the addition salt in the water-alcohol dispersion ranges from 1 to 10% approximatively, preferably from 3 to 5%.

The dispersion is kept at a temperature equal to or around that of reflux. Furthermore, the dispersion is kept under low stirring, to prevent the mechanical disintegration of the forming crystals. The hydrochloric acid used to displace the organic acid from its addition salt to obtain ziprasidone hydrochloride is diluted hydrochloric acid in water-alcohol mixture as indicated above, to a concentration preferably ranging approx. from 5 to 20%.

Preferably, hydrochloric acid is added in two subsequent portions: after the first addition, the mixture is seeded with ziprasidone hydrochloride, keeping the temperature of the dispersion around or at the reflux. For example, a first addition of approx. 0.5 equivalents of HCl is carried out to form the first crystalline seeds, then a second addition of a further 1.5 equivalents of HCl is performed in a time preferably ranging from approx. 2 to 2.5 hours to complete crystallization. Under these conditions, crystalline particles having mean diameter around 150 μm are obtained.

The size of the resulting particles is a function of the addition rate of the hydrochloric acid second portion. In fact, when the second addition of HCI is carried out in a longer time, e.g. about 5 hours, the resulting ziprasidone hydrochloride crystalline particles are larger, typically approx. from 150 to 400 μm.

After completion of the HCl addition and cooling to a temperature equal to or lower than approx. 30° C., preferably 15 to 25° C., the solid product can be recovered by known procedures, such as filtration or centrifugation, followed by washing with the same alcoholic solvent as used above, and finally drying under vacuum at a temperature of 70° C. to constant weight. If desired, the resulting particles can be subjected to procedures to reduce their size, such as grinding.

The resulting anhydrous ziprasidone hydrochloride free from colored impurities can optionally be isolated as indicated above, then converted to the free base or to another pharmaceutically acceptable salt thereof according to known methods. For example, the conversion to the base can be carried out by treatment with a basic agent, typically ammonia or a primary amine, e.g. methylamine, a secondary amine, e.g. dimethyl- or diethyl- amine, or a tertiary amine, e.g. triethylamine or tributylamine. Likewise, the conversion of the base to an anhydrous or hydrate salt thereof can be carried out with known methods, for example as described in U.S. Pat. No. 4,831,031; U.S. Pat No. 5,321,925; U.S. Pat No. 6,110,918 and WO 97/42191.

Therefore, the invention provides a process for the purification of ziprasidone to obtain ziprasidone as the free base, or a salt thereof, with purity degree equal to or higher than 99.9% and free from residual colored impurities, so that it fulfils the regulatory requirements for therapeutical products.

Anhydrous ziprasidone hydrochloride in the form of particles having mean diameter above 85 μm, as obtainable by the process of the invention, shows higher resistance to the absorption of atmospheric humidity.

FIG. 2 shows the comparison between two samples of anhydrous ziprasidone hydrochloride, one known and having D[4,3] of 50 μm and the other. according to the invention, having D[4,3] of 150 μm, both samples having been exposed at 25° C. in environment with 50% relative humidity.

The properties of anhydrous ziprasidone hydrochloride of the invention can be advantageously exploited in the work up, transport, storage and pharmaceutical technique for the preparation of novel formulations of said product.

A further object of the invention is therefore anhydrous ziprasidone hydrochloride having purity degree equal to or higher than 99.9%, free from residual colored impurities, particularly in the form of particles having mean diameter above 85 μm.

A further object of the invention is a pharmaceutical composition comprising a suitable carrier and/or excipient and as the active ingredient ziprasidone base, or a pharmaceutically acceptable salt thereof, free from colored impurities.

A pharmaceutical composition can be formulated according to known techniques. The dosage of active ingredient in the single pharmaceutical formulations, such as capsules, tablets, sugar-coated pills or other forms for the unitary administration through the oral route, approximatively ranges from 15 to 80 mg.

The following examples illustrate the invention.

EXAMPLE 1

Preparation of Ziprasidone Camphorsulfonate

A 2 liters round-bottom four necked flask, equipped with mechanical stirrer, reflux condenser and thermometer, is loaded with 61 g of ziprasidone free base and 1110 ml of methanol. The suspension is heated to a temperature of 60-65° C. and a solution of 36.03 g of (S) camphorsulfonic acid in 90 ml of methanol is added thereto, under stirring. The resulting suspension is cooled to a temperature of approx. 5-20° C., filtered on a Buckner funnel, the solid is washed with methanol (2×30 ml) on the filter and dried in a static dryer at a temperature of 50° C. to constant weight. 85 g (S) of ziprasidone camphorsulfonate are obtained.

EXAMPLE 2

Preparation of Anhydrous Ziprasidone Hydrochloride

A 2 liters round-bottom four necked flask, equipped with mechanical stirrer, reflux condenser and thermometer, is loaded with 60 g of ziprasidone camphorsulfonate, 1440 ml of methanol and 360 ml of water. The dispersion is heated to a temperature of approx. 70-71° C. to obtain a clear solution, which is then stirred at 80 rpm with mechanical stirrer, seeded with anhydrous ziprasidone hydrochloride and added first with about 5.5 g of 37% HCl diluted in 55 ml of methanol in approx. 10 seconds. The solution becomes turbid as the first crystalline seeds form. Stirring is increased to 120 rpm and the solution is added with 10.09 g of 37% HCl diluted in 50 ml of methanol during the two subsequent hours, thereby completing crystallization. After completion of the acid addition, the suspension is cooled to 20° C., filtered on a Buckner funnel and the solid is washed on the filter with acetone (2×100 ml). The resulting wet product is then dried in a static dryer under vacuum at 70° C to constant weight, thereby obtaining 36 g of anhydrous ziprasidone hydrochloride, having 0.10% water content (Karl-Fischer), 99.9% purity degree [HPLC], free from colored impurities, in the form of particles having D[4,3] of approx. 150 µm and particle size distribution characteristics substantially as shown in FIG. 1.

Following the same procedure, but prolonging the time of the second addition of 37% HCl, particles having size approx. ranging from 150 to 400 µm, 0.10% water content (Karl-Fischer), 99.9% purity degree [HPLC] and free from colored impurities, are obtained, depending on the addition time.

The invention claimed is:

1. Ziprasidone camphorsulfonate, either as a single (S) or (R) enantiomer or as a racemic mixture thereof:

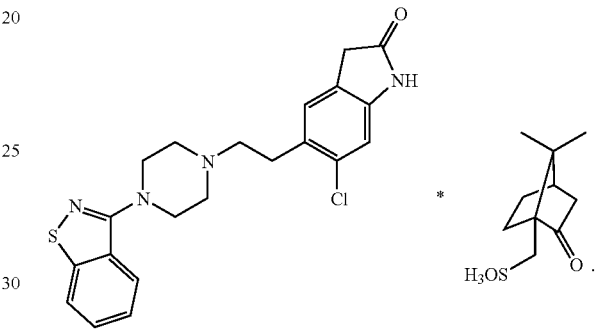

\* \* \* \* \*